US008614794B2

(12) United States Patent
Smith et al.

(10) Patent No.: US 8,614,794 B2
(45) Date of Patent: Dec. 24, 2013

(54) SYSTEM AND APPARATUS FOR MONITORING CONCENTRATION OF GREENHOUSE GAS

(75) Inventors: Patrick L Smith, Arroyo Grande, CA (US); Steven M Beck, Palos Verdes Estates, CA (US)

(73) Assignee: The Aerospace Corporation, El Segundo, CA (US)

( * ) Notice: Subject to any disclaimer, the term of this patent is extended or adjusted under 35 U.S.C. 154(b) by 114 days.

(21) Appl. No.: 13/299,073

(22) Filed: Nov. 17, 2011

(65) Prior Publication Data

US 2013/0128271 A1    May 23, 2013

(51) Int. Cl.
*G01N 21/00* (2006.01)
*G01N 21/39* (2006.01)

(52) U.S. Cl.
CPC ..................................... *G01N 21/39* (2013.01)
USPC .......................................................... 356/437

(58) Field of Classification Search
CPC ............................... G01N 21/00; G01N 21/39
USPC ................................................... 356/432–442
See application file for complete search history.

(56) References Cited

U.S. PATENT DOCUMENTS

| | | | |
|---|---|---|---|
| 3,788,742 A | 1/1974 | Garbuny | |
| 5,604,595 A * | 2/1997 | Schoen | 356/432 |
| 5,898,373 A * | 4/1999 | Murad et al. | 340/600 |
| 6,061,141 A * | 5/2000 | Goldenberg et al. | 356/437 |
| 6,853,452 B1 * | 2/2005 | Laufer | 356/436 |
| 7,224,905 B2 * | 5/2007 | Ruggiero | 398/170 |
| 7,352,463 B2 | 4/2008 | Bounaix | |
| 7,523,638 B2 | 4/2009 | Prince | |
| 7,743,643 B2 | 6/2010 | Prince | |
| 7,934,412 B2 | 5/2011 | Prince | |
| 7,953,558 B2 | 5/2011 | Burba et al. | |
| 8,269,971 B1 * | 9/2012 | Marsh et al. | 356/437 |
| 2005/0039515 A1 | 2/2005 | Prince | |
| 2006/0119851 A1 | 6/2006 | Bounaix | |
| 2007/0215795 A1 | 9/2007 | Kameyama et al. | |
| 2009/0055102 A1 | 2/2009 | Laufer et al. | |
| 2009/0133465 A1 | 5/2009 | Prince | |
| 2009/0139299 A1 | 6/2009 | Prince | |
| 2009/0273781 A1 | 11/2009 | Clegg et al. | |
| 2010/0198736 A1 | 8/2010 | Marino | |

OTHER PUBLICATIONS

Proschek et al., Greenhouse Gas Profiling by Infrared-Laser and Microwave Occultation: Retrieval Algorithm and Demonstration Results from End-to-End Simulations, Apr. 21, 2011, Published by Copernicus Publications on behalf of the European Geosciences Union.

(Continued)

*Primary Examiner* — Michael P Stafira
(74) *Attorney, Agent, or Firm* — LeonardPatel PC (57) ABSTRACT

One or more embodiments of the present invention pertain to a system, method, and apparatus that accurately measures concentration of a greenhouse gas in narrow atmospheric columns above multiple sites utilizing a network of autonomous low-cost beacons that turn on for short unannounced time intervals and point to a receiving satellite. For example, each beacon can activate for short time intervals and transmit a laser beam at eye-safe low transmission power levels to a receiving satellite. The receiving satellite includes a sensor configured to receive the laser beam from one or more activated beacon and generate raw greenhouse gas concentration data based on measurement of the received laser beam intensity at selected wavelengths.

21 Claims, 4 Drawing Sheets

(56) References Cited

OTHER PUBLICATIONS

A. Hollingsworth, GEMS: Global Earth-System Monitoring using Space and in-situ data, Apr. 2005.

Nakajima et al., Monitoring of the Greenhouse Gases from Space by GOSAT, 2010, International Archives of the Photogrammetry, Remote Sensing and Spacial Information Science, vol. XXXVIII, Part 8, Kyoto Japan.

Humphreys et al., Sodium-Layer Synthetic Beacons for Adaptive Optics, The Lincoln Laboratory Journal, vol. 5, No. 1, 1992.

Sugimoto et al., Theoretical Evaluation of Earth-to-Satellite Laser Long-Path Absorption Measurement of Atmospheric Trace Species in the Infrared Region, Mar. 18, 1995, National Institute for Environmental Studies, Japan.

* cited by examiner

SYSTEM AND APPARATUS FOR MONITORING CONCENTRATION OF GREENHOUSE GAS

FIELD

The present invention relates to a worldwide greenhouse gas monitoring system and, more particularly, to a worldwide greenhouse gas monitoring system that uses laser ground beacons and satellites.

BACKGROUND

Climate researchers and policy makers have raised concerns that there are no current or planned means to independently verify a nation's self-reported greenhouse gas (GHG) emissions inventory with sufficient accuracy to verify compliance with emission limits in future treaties or provide agencies responsible for administrating future carbon markets the ability to detect underreporting and misleading accounting. Mistrust of nations' self-reports is becoming a stumbling block in efforts to agree on more stringent carbon-reduction targets. Poorer nations cannot afford extensive in situ monitoring networks. And some nations are reluctant to allow on-site inspection or disclose economic proxy data.

Existing atmospheric carbon dioxide ($CO_2$) sampling stations are not able to monitor emissions from large local sources or verify national emission inventories. In fact, existing in situ sensors are purposefully sited away from fossil fuel emission sources in order to better monitor natural sources and sinks for research purposes. Deploying a sufficient number of additional in situ GHG sensors for monitoring national emissions, though physically possible, would be extremely costly and require on-site personnel for maintenance and operation. Also, in situ sensors are vulnerable to tampering and vandalism. Nor is a constellation of satellites with sensors capable of measuring GHG emissions with sufficient accuracy and spatial resolution sufficient to independently verify nations' compliance with future treaty limits practical or affordable.

SUMMARY

Certain embodiments of the present invention may provide solutions to the problems and needs in the art that have not yet been fully identified, appreciated, or solved by current GHG monitoring systems. For example, one or more embodiments of the present invention pertain to an independent means for accurately verifying nations' self-reported GHG emissions inventory. A world-wide network of low-cost autonomous ground laser beacons can be commanded by a central command center (or authority) to briefly turn on at unannounced (or random) times and point to a receiving satellite equipped with a sensor and processor that accurately determines concentrations of GHG in the atmospheric columns through which the beams pass. All data collection functions can be centralized in the satellite receiver and the data can be transmitted to a command center for processing. The solar powered beacons require no outside wiring connection and can receive operating commands at very low data rates from a centralized network control node via cell or other local networks.

In accordance with an embodiment of the present invention, a system is provided to monitor concentration of one or more gases. The system includes a plurality of beacons, where each beacon activates for short unannounced time intervals, and transmits a laser beam at low transmission power levels to a receiving satellite. The receiving satellite includes a sensor that receives the laser beam from one or more activated beacons and generates raw gas concentration data based on the laser beam.

In yet another embodiment of the present invention, an apparatus is provided. The apparatus includes a laser unit. The laser unit activates for short unannounced time intervals based on a command received from an electrical unit. When the laser unit is activated, the laser unit generates a laser beam to be transmitted to a satellite in order to measure concentration of a gas in an atmospheric column through which the laser beam passes.

In yet another embodiment of the present invention, a method for monitoring a concentration of the one or more gases is provided. The method includes receiving an activation signal from a node for monitoring the concentration of the one or more gases. The method includes transmitting a laser beam from a beacon to a receiving satellite in order to determine the concentration level of the one or more gases in an atmospheric column through which the laser beam passes.

BRIEF DESCRIPTION OF THE DRAWINGS

For a proper understanding of the invention, reference should be made to the accompanying figures. These figures depict only some embodiments of the invention and are not limiting of the scope of the invention. Regarding the figures.

DETAILED DESCRIPTION OF THE EMBODIMENTS

It will be readily understood that the components of the invention, as generally described and illustrated in the figures herein, may be arranged and designed in a wide variety of different configurations. Thus, the following detailed description of the embodiments is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with an embodiment may be included in at least one embodiment of the invention. Thus, appearances of the phrases "in certain embodiments," "in some embodiments," "in other embodiments," or other similar language, throughout this specification do not necessarily all refer to the same embodiment or group of embodiments, and the described features, structures, or characteristics may be combined in any suitable manner in one or more embodiments.

One or more embodiments described herein pertain to a hybrid combination of ground and space components to monitor a nation's GHG emissions inventory. For instance, low-cost ground laser beacons can be sited throughout each country on a regular grid and additional beacons can be located near emission sources such as power plants. It is the geo-proximity between the beacon and the site under consideration that allows the correlation between column GHG concentration and site emission rate. Each beacon can be individually commanded by a network control node (or a central command center). For example, a beacon can be commanded to activate (or turn on) at unannounced (or random) time intervals and transmit a laser beam at a satellite receiver. Concentrations of GHG in the atmospheric columns through which the beams pass are determined from the measured relative attenuation of the spectral lines in the received laser signal.

Figure 1:
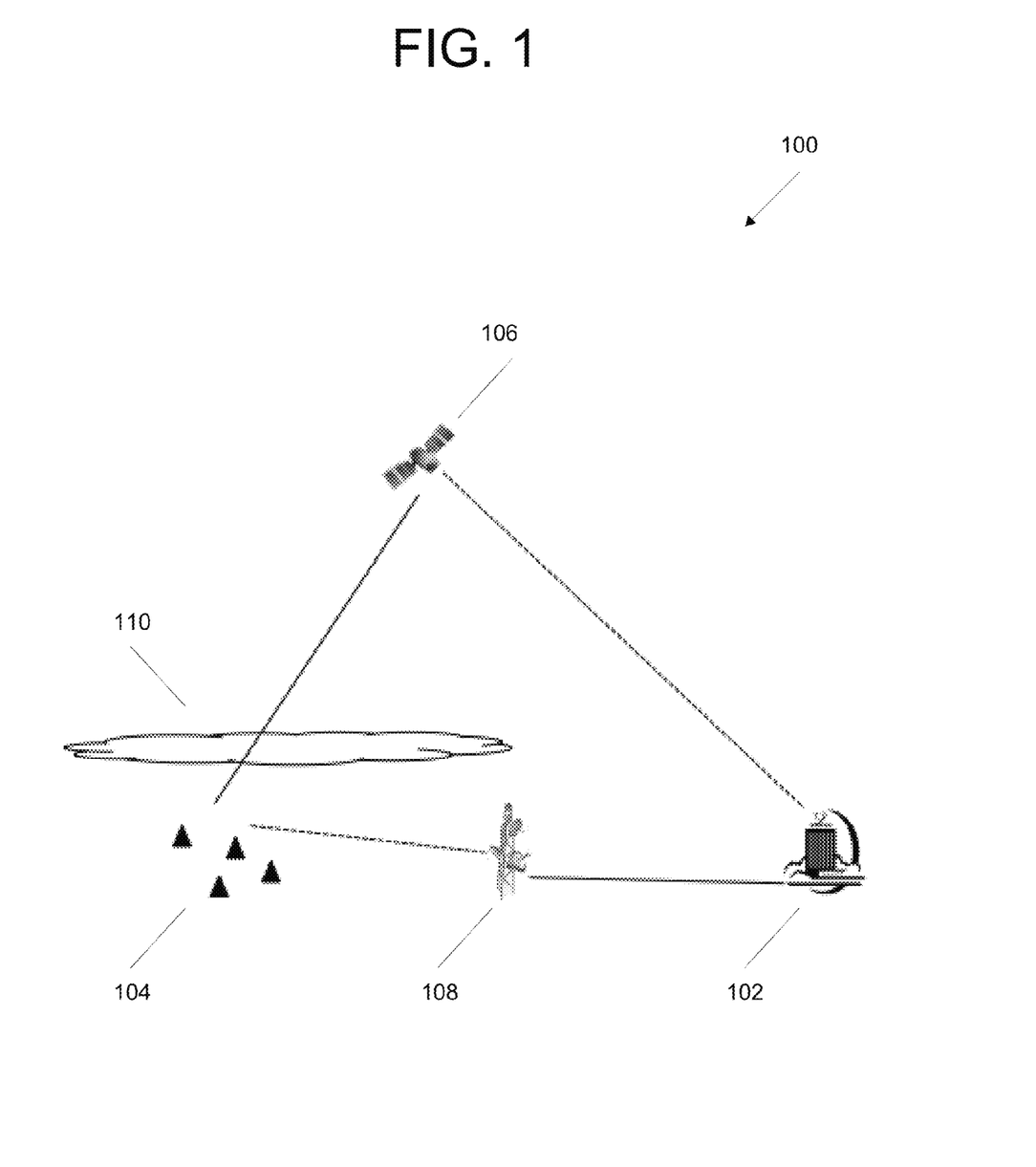
FIG. 1 illustrates a greenhouse gas concentration monitoring system, in accordance with an embodiment of the present invention.

FIG. 1 illustrates a greenhouse gas concentration monitoring system 100, in accordance with an embodiment of the present invention. System 100 includes, but is not limited to, a processing and control center (or node) 102, a plurality of laser beacons 104 distributed throughout a particular country or globally distributed throughout the world, at least one satellite receiver (or receiving satellite) 106, and at least one satellite, cellular, WIFI or other communications network 108. When a beacon 104 is added to system 100, the Internet, cell or other network address and the location of beacon 104 are added in a database at control center 102. It should be appreciated that the number of beacons 104 may be increased or decreased and the position of one or more of the beacons are easily changed in this manner.

In this embodiment, control center 102 can transmit a signal containing a message to one or more of laser beacons 104 via the cellular, WIFI or other network 108. The signal containing the message instructs at least one of laser beacons 104 to activate for a specified time interval and transmit a laser beam through atmosphere 110 to a satellite receiver 106. The activation time interval can be very short: 15 seconds, 1 minute, 5 minutes, or any time period that is sufficient to accomplish greenhouse gas concentration measurement. It can be appreciated that the narrow laser beam, as it rises up through the lower atmosphere, provides much finer spatial resolution than a satellite-based imaging sensor pixel footprint. Also, the laser beam can be modulated to make the received signal more detectable against background noise. The laser beam can also be modulated to encode information to identify the particular beacon and relay beacon operation and status information. Also, the laser can provide significantly smaller frequency bandwidths allowing higher spectral resolution than can passive satellite hyperspectral imagers. This is an advantage for discriminating one GHG species from another or from backgrounds.

It should be appreciated that there are several considerations in order to determine when to activate one or more of laser beacons 104. For example, if system 100 utilizes three geosynchronous satellites, each laser beacon 104 is always in the view of at least one of the geosynchronous satellites (excepting in the far polar regions) and can be accessed at any time depending on cloud cover. Another consideration can be how frequently beacons 104 need to be accessed by each satellite and how long beacons 104 would have to remain activated in order to achieve the required measurement accuracy.

Beacons 104 can also be activated based on the requirements of the GHG emissions treaty and the past history of treaty compliance in the region or at the beacon site. For example, if a particular city is being monitored for concentration of a greenhouse gas, then control center 102 can activate beacons 104 located within and around the city several times a day to obtain measurements of the greenhouse gas concentration level and determine compliance with treaty provisions. However, for example, if a coal power plant is being monitored for concentration of a greenhouse gas, then control center 102 can activate one or more of beacons 104 located around the coal power plant to measure the greenhouse gas concentration level and determine compliance. In other words, in order to determine when to activate beacons 104, system 100 considers the number (or density) of beacons 104, the temporal or diurnal variation of the GHG being measured, the country that is being monitored, etc. It should be noted that because the country, place, etc., being monitored would not know when beacons 104 are being activated, the measurements being obtained are more reliable and accurate for the purpose of determining treaty verification and compliance.

Satellite receiver 106 can be a dedicated satellite to monitor concentration of GHG having a dedicated sensor and dedicated downlink transmitter in order to downlink data to control center 102. In another embodiment, satellite receiver 106 can be a military, civil or commercial satellite which serves as a host for a separate payload equipped with a sensor and interface to receive data that is transmitted or routed to control center 102.

Satellite receiver 106 can then obtain raw data pertaining to the concentration of the greenhouse gas and transmit the raw data for processing to control center 102. For example, the raw data can be downlinked to control center 102, which can analyze the data and generate more beacon activation commands. Because satellite receiver 106, and not beacon 104, collects the data, system 100 is simpler, more reliable and secure than current in situ GHG monitoring stations. Also, all data collection and signal processing can be centralized in satellite receiver 106.

The raw data may be processed on-board satellite 106 and the result downlinked to control center 102 or the raw data may be downlinked and the processing carried out on the ground. The raw data obtained by the satellite sensor can include location specific laser beam intensity and/or phase for at least two wavelengths, as well as on and off the molecular resonance of the GHG species being monitored. In addition, the phase and/or intensity of the laser beams as they exit beacon 104 are measured and those values linked to satellite 106 directly or to control center 102 via cell phone, WIFI Internet connection, fiber or other network. The ratio of intensities of the two wavelengths before transiting the atmosphere and at the satellite sensor after transiting the atmosphere constitutes the raw data from which the GHG column density is determined. The off resonance wavelength, which is chosen to be close to the on-resonance wavelength, provides a reference that serves to eliminate the common path extinction not due to the GHG of interest. The processing of the raw intensity data follows standard long-path differential absorption methods. An alternative to measuring the relative intensities of the two wavelengths of the laser beams as they exit beacon 104 would be to generate the two wavelengths in such a manner as to guarantee that the intensity ratio is known and constant. One possible means of doing this would be to generate the two wavelengths as upper and lower frequency side bands to a carrier by modulation of the carrier and use just the side bands as the two wavelengths. The fact that the two sidebands are generated from the common carrier locks their intensity ratio, regardless of their absolute intensity.

Since the laser beams are narrow frequency coherent light sources their phase is well defined. The phase of the beams can be measured using standard heterodyne methods and the relative phase before and after transit through the atmosphere carries information about the interaction of the light and the atmosphere. If both wavelengths are not resonant with any atmospheric species, and they co-propagate through the atmosphere, they will experience almost identical perturbation to their phase. Therefore, the relative phase of the two wavelengths stays constant. If, however, one of the wavelengths is resonant with a GHG, it will experience a phase shift relative to the non-resonant wavelength. This phase shift difference can be measured and ultimately related to the column density of the GHG constituent.

From the processing performed by control center 102 using the sensor data down linked to control center 102, the concentration of GHG can be derived in the column of atmosphere 110 through which laser beam is passed from laser beacon 104 to satellite receiver 106. This provides a precise measurement of the concentrations in gases in the atmosphere above at sites where beacons 104 are located.

It should be appreciated that system 100 can also allow measurements of isotopic abundance in a column at high spatial resolution.

It should also be appreciated that the low-cost ground beacons can be repositioned as required and proliferated without substantially affecting or burdening the data and control communications architecture. Also, the laser beacons can be inherently less expensive to build, operate and maintain and more tamper resistant than current in situ sensors.

It should be appreciated that natural sources and anthropogenic sources can also be measured by system 100. In other words, system 100 can measure and distinguish between natural sources of $CO_2$ and anthropogenic sources (e.g., fossil fuels) of $CO_2$.

Figure 2:
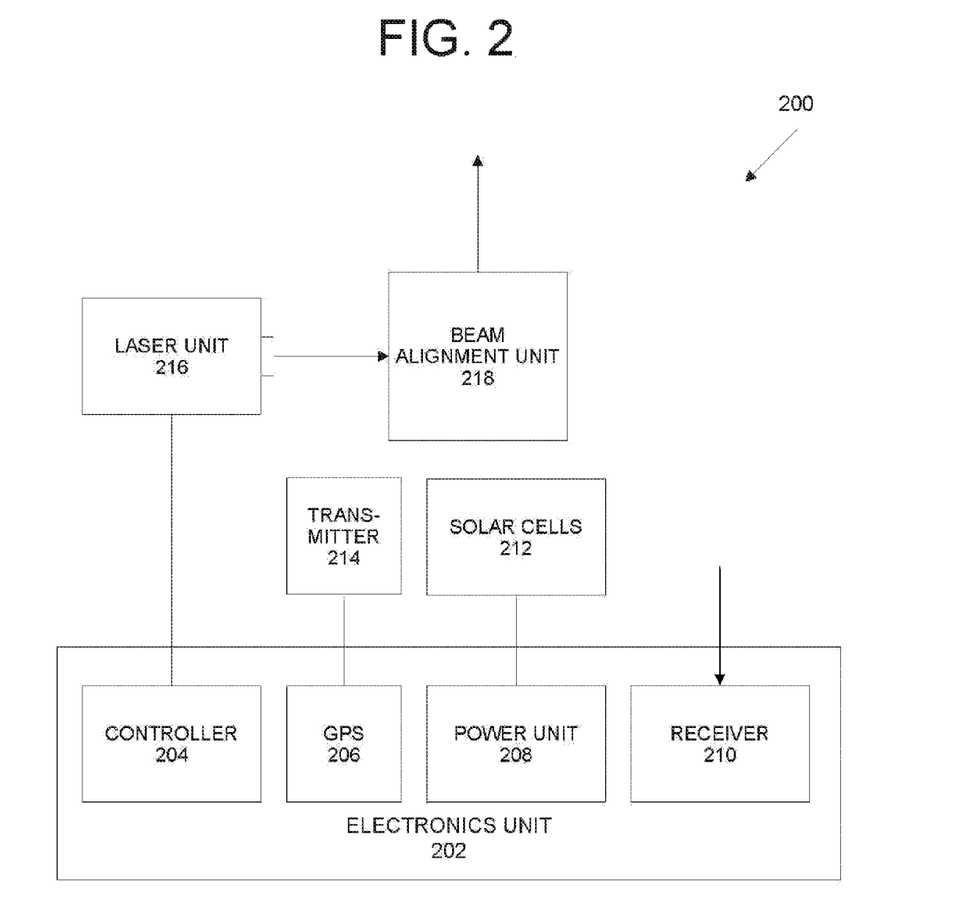
FIG. 2 illustrates a beacon, in accordance with an embodiment of the present invention.

FIG. 2 illustrates a beacon 200, in accordance with an embodiment of the present invention. In one or more embodiments, beacon 200 may be autonomous and self-contained, requiring no wiring connections or on-site maintenance. Beacon 200 can be mounted to a building or structure, a telephone pole, an electric pole, roof railing, base station, or any location that would provide a stable platform and be appreciated by a person of ordinary skill in the art. Beacon 200 can be weather proofed to sustain the rigors of a harsh climate. Beacon 200 can be installed and initially aligned by technicians with training comparable to a satellite TV installer. No external wiring or other connections are required in some embodiments.

When beacon 200 is installed and aligned initially, its location and Internet, cell or other network address is identified to a control center. In order to initially align beacon 200, a beam alignment unit 218 may be used to maximize the signal strength received by the receiving satellite.

It should be noted that a precise alignment calibration of beacon 200 is determined using a procedure such as the following. For example, initial alignment of the laser beam may be accomplished during setup using celestial alignment tools and a gimbal mount pointing model. Boresighting of the laser beams to the gimbal pointing can also be accomplished during the initial setup using beam alignment tools such as retro-reflectors and focal planes. Precise time may be determined from Global Positioning System (GPS) 206 on beacon 200. After installation and during beacon operation when the satellite receives the laser beam transmitted by beacon 200, beacon 200 can execute a slight angular dither motion of the laser beam pointing mechanism to provide a means to finely adjust pointing alignment to maximize the received signal strength. In one embodiment, if, during a subsequent operation, beacon 200 becomes misaligned and cannot be detected by the receiving satellite, the initial alignment procedure can be repeated. In another embodiment, if beacon 200 has malfunctioned or knocked substantially out of alignment, or a combination thereof, then control center can detect that beacon 200 is inoperable and deactivate beacon 200 until a replacement beacon is installed or beacon 200 can be realigned.

Beacon 200 includes an electronics unit 202. Electronics unit 202 includes, but is not limited to, a controller 204 having a processor, GPS 206, a power unit (which includes a battery or other energy storage device) 208, and a cell, WIFI or other network receiver 210.

GPS 206 determines the location of beacon 200, which is identified to a control center. Power unit 208 is operatively connected to a power source, such as solar cells 212, in order to charge a battery or other energy storage device in power unit 208. Because beacon 200 can be solar powered, beacon 200 does not require power from an electric grid, communication grid or other external power source. Short duration laser operation and continuous solar power during daylight hours allow beacon 200 to operate at low average power levels of approximately 1 watt or less. However, it should be appreciated that beacon 200 can operate at any power level that would be sufficient to accomplish GHG concentration measurements.

Receiver 210 may be a standard cellular, WIFI or other network receiver. Signals are transmitted via the communications network or Internet to command or instruct beacon 200 when to activate. In one or more embodiments, receiver 210 may receive an activation instruction based on a desired rate of sampling of GHG gas concentrations in a particular region, an optimum slew schedule for a low earth orbiting (LEO) receiving satellite, suspected greenhouse gas concentration violations at the site, the number of beacons in surrounding region that may also need to be accessed, weather forecasts over regions, and/or periods when a LEO receiving satellite is in view.

Beacon 200 also includes a laser unit 216 that is operatively connected to electronics unit 202 and beam alignment unit 218. Beam alignment unit 218 includes a pointing mechanism (not shown) configured to point or accurately align the laser beam generated from laser unit 216 and transmit the laser beam to a receiving satellite. For a LEO receiving satellite, which is constantly moving relative to the earth's surface, beam alignment unit 218 can be constantly tracking the satellite during the period when the laser beam is generated and transmitted to the receiving satellite. In another embodiment, beam alignment unit 218 can self-align when beacon 200 is activated by the control center. It should be appreciated that the laser beams generated by laser unit 216 may be eye-safe low-power laser beams, which alleviates the concern of endangering people, aircraft, birds, etc. It should be appreciated that the laser beam operates at a low transmission power level of approximately 1 watt or less. However, the transmission power level of the laser beam may be set to any level that would be appreciated by a person of ordinary skill in the art.

In some embodiments, it should be noted that a boresighting realignment mechanism can be used to compensate for thermal changes or other slight misalignments that can occur mechanically. It should be appreciated that the use of a bore-sighting realignment mechanism is a design choice, and other mechanisms may be used by a person of ordinary skill in the art.

It should be appreciated that laser beacon 200 relies on differential absorption of two or more laser frequencies for the GHG molecule of interest, such as $CO_2$, methane, nitrous oxide ($N_2O$), etc. In this embodiment, laser unit 216 can generate simultaneously or alternatively two or more narrow frequencies of light to form a laser beam based on the molecule of interest. For example, one frequency of light can be tuned to a molecular absorption feature ($\lambda_{on}$) and another frequency of light can be close in frequency, but off the molecular resonance ($\lambda_{off}$). The two frequencies can be chosen to fulfill several requirements. For example, the frequencies should not be strongly absorbed by water or other prominent atmospheric species. Also, the resonant frequency ($\lambda_{on}$) should coincide with an absorption feature of the molecular species of interest, but not so strong of an absorption feature that the laser beam is attenuated below the detection limit of the receiver sensor. If necessary, additional frequencies that measure oxygen, nitrogen, or any other desired atmospheric gas can provide a reference to compensate for atmospheric temperature and density effects. Laser unit 216 can include a multiplexor to combine the two or more frequencies in order to transmit the laser beam to the receiving satellite.

In an alternative embodiment, the laser beam intensity can be encoded with information by chopping the beam or modulating the beam intensity without disturbing the intensity difference between the two or more frequencies of interest to allow information to be transmitted from beacon 200 to the satellite and then to the control center. By encoding information on the laser beam, the system can avoid transmitting the information back using the cellular, WIFI or other network, which could potentially be spoofed or be intercepted on the ground in an undetected manner. The information encoded on the laser beam can be a measurement of the laser beam intensity and/or phase at the exit of beacon 200, which can provide increased GHG measurement accuracy when combined with measurement of received intensity and/or phase at the satellite sensor. The information encoded on the laser beam can also include the GPS coordinates of beacon 200, temperature of beacon 200, atmospheric temperature, beacon power system status, or any available information that would be appreciated by a person of ordinary skill in the art.

In another embodiment, beacon 200 may include a tracker that allows pointing a laser beam at, for example, a LEO satellite for a period of 5 seconds, 10 seconds or any period when the satellite is in view of the beacon. Beacon 200 may also include an aperture cover that pops open for the brief time when the laser is operating and closes when the laser is not operating to protect beacon optics from dust and moisture. A sensor (not shown in the drawings) can be mounted on the outside of beacon 200 that can abort beacon operation by leaving the aperture cover closed if the sensor senses that it is raining, cloudy, and/or foggy. Aborted operational periods can be recorded and information can be transmitted at a later time to inform the control center when beacon operations were aborted.

Figure 3:
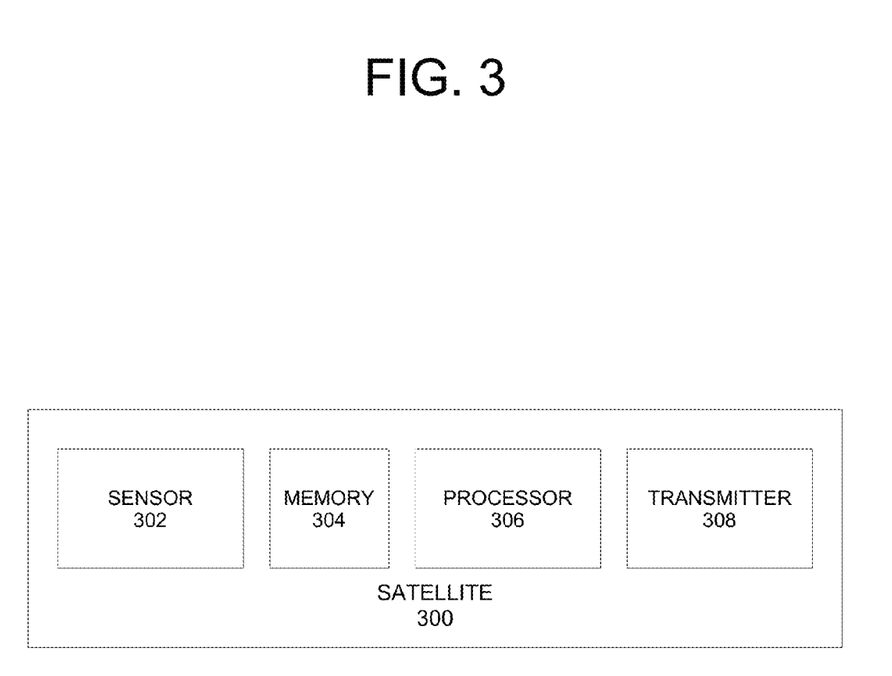
FIG. 3 illustrates a satellite, in accordance with an embodiment of the present invention.

FIG. 3 illustrates a satellite 300, in accordance with an embodiment of the present invention. In one or more embodiments, satellite 300 may be in any suitable orbit, such as a LEO or a geostationary or geosynchronous orbit (GEO). If the system utilizes a GEO satellite, then the system may utilize approximately three GEO satellites for worldwide coverage, excluding the far Polar Regions. If a LEO satellite is used, then the system may utilize one or more LEO satellites. In the case where a LEO satellite is used, the LEO satellite utilizes a gimbaled sensor that selectively points to the beacons as the LEO satellite is passing over or alternatively has a sensor with a wide field of view capable of detecting laser beams emanating anywhere within a large swath over which the sensor travels or passes. In some embodiments, the beacons can have a gimbaled pointing and tracking mechanism to continuously point the laser beam at a LEO satellite as it passes in view. In other embodiments, the laser beam is spread over a wide field of view to allow the beam to dwell on the LEO satellite for a sufficient period to achieve the required measurement accuracy. It should be appreciated that a LEO satellite allows measurement of gases in far Polar Regions. Also, because the laser beam is continuously slewing to point to the LEO satellite, a different column of air is being sampled as the LEO satellite passes over.

Satellite 300 includes, but is not limited to, a sensor 302, memory 304, processor 306, and transmitter 308. Sensor 302 is configured to receive laser beam from one or more beacons and store information pertaining to the laser beam in memory 304. For example, the information can include raw laser intensity and/or phase measurements for the molecule or species of interest, information encoded in the laser beacon, etc. In one or more embodiments, sensor 302 can generate GHG column density data based on the measured intensity of the received laser beam. Transmitter 308 can then transmit the information to the control center for processing and for ultimately determining whether a particular place (facility, country, etc.) is in compliance with the greenhouse gas emissions requirements. In the case where a GEO satellite is used, there may be a continuous downlink to the central control for data communications. In the case where a LEO or other nongeosynchronous orbit satellite is used, the information can be stored and transmitted when a ground station comes in view or relayed via other satellites to a ground station.

Figure 4:
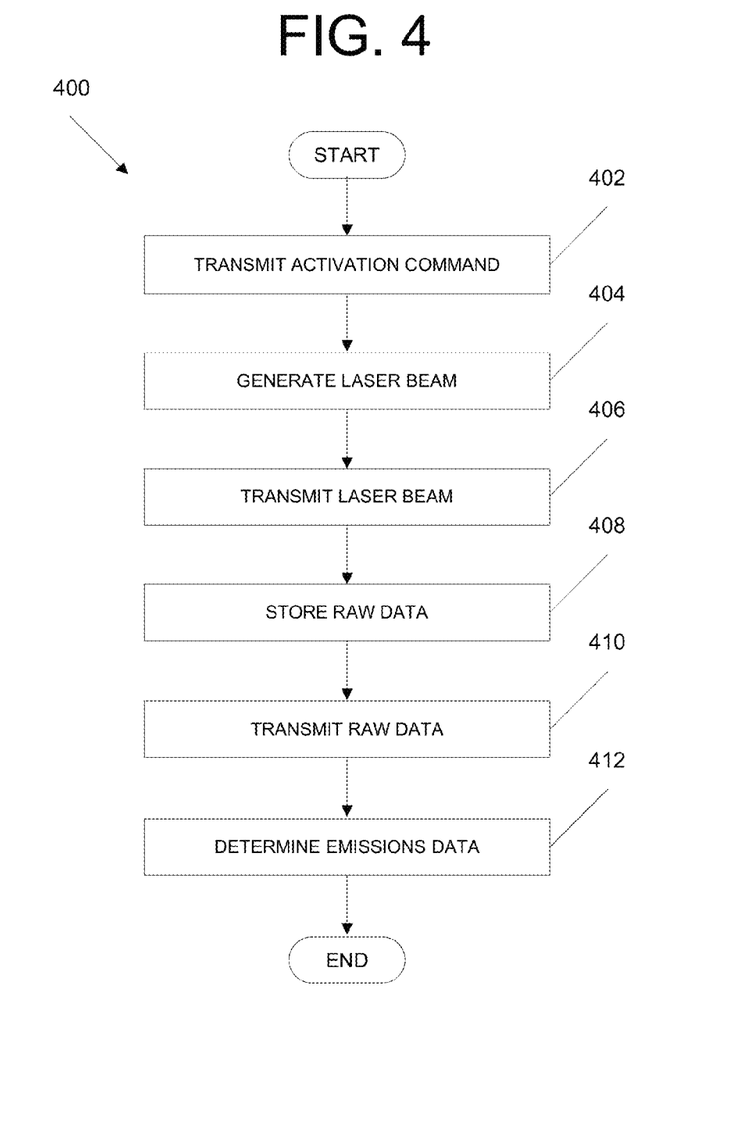
FIG. 4 illustrates a method for monitoring greenhouse gas concentration, in accordance with an embodiment of the present invention.

FIG. 4 illustrates a method for determining GHG concentration, in accordance with an embodiment of the present invention. At 402, a control center transmits an activation command to one or more beacons. Activation intervals can be unannounced (or sent at random times) and can be based on requirements set by a treaty in order to gather greenhouse gas concentration data to monitor greenhouse gas emissions in a certain country, facility, etc. Upon activation, the one or more beacons can generate at 404 a laser beam. The laser beam includes two or more frequencies based on the molecule or species of interest.

At 406, the one or more beacons transmit the generated laser beam to the receiving satellite in order to accurately determine concentration levels of GHG in the atmospheric columns through which the laser beam passes. At 408, a sensor of the receiving satellite receives the laser beam and generates raw data pertaining to concentration levels of GHG in the atmospheric columns. At 410, the raw data is transmitted from the receiving satellite to the control center and the raw data is processed at 412 to determine concentration levels of GHG in the atmospheric columns.

The method steps shown in FIG. 4 may be performed, in part, by a computer program, encoding instructions for a nonlinear adaptive processor to cause at least the methods described in FIG. 4 to be performed by the apparatuses discussed herein. The computer program may be embodied on a non-transitory computer readable medium. The computer readable medium may be, but is not limited to, a hard disk drive, a flash device, a random access memory, a tape, or any other such medium used to store data.

The computer program may include encoded instructions for controlling the nonlinear adaptive processor to implement the method described in FIG. 4, which may also be stored on the computer readable medium. The computer program can be implemented in hardware, software, or a hybrid implementation. The computer program can be composed of modules that are in operative communication with one another, and which are designed to pass information or instructions to display. The computer program can be configured to operate on a general purpose computer, or an application specific integrated circuit ("ASIC").

It should be noted that since $CO_2$ is a linear molecule, it does not have a permanent dipole moment and, therefore, it has no pure rotational spectrum and cannot be detectable by microwave radiometers. Remote sensing of $CO_2$ from space depends upon using infrared (IR) passive sensors to detect its IR spectrum. Such IR sensors cannot work from a GEO platform due to their poor spatial resolution. IR sensors on LEO platforms are significantly limited due to their sensitivity to the presence of clouds in their field of view. Clouds preclude accurate atmospheric column $CO_2$ concentration measurements by passive IR sensors. Therefore, data acquisition is limited to a relatively small fraction of the LEO orbit period, which is free of clouds. This coupled with a long revisit time for a LEO satellite makes it very difficult to monitor a specific region from LEO orbits with high temporal resolution. The beacon system can rely on a GEO platform mounted sensor, so while for any specific time period clouds can be a problem, the fact that the satellite is constantly in view of the beacon allows ample opportunity to experience a cloud-free line of sight from the beacon to the satellite. The narrow path of the laser beam as already described provides a much greater spatial resolution than passive IR sensors.

As required in the current Kyoto treaty, some countries currently self-report their emissions inventories. Currently, there is no independent check on the levels of greenhouse emissions being self-reported by these countries. The embodiments described herein provide the people who are planning and negotiating future GHG emissions agreements and treaties with another option and tool for verifying the compliance with the future treaty provisions. In other words, the system described herein can facilitate treaty planning and negotiations because the system provides a feasible and more affordable means to monitor and encourage compliance with treaty provisions and because the system is relatively tamper-proof. It should be appreciated that the beacons are self-contained (e.g., no outside connection) and do not require onsite personnel for operation and maintenance.

Some countries are concerned with satellites potentially collecting data not directly related to treaty provisions. Because beacons are specifically used only in conjunction with the satellites to measure certain specific gases at certain specific sites, and are not able to collect other types of data and all the collected data is controlled and protected by a central agency such as the United Nations, a country may be less concerned with the perceived risk of potential intrusive satellite surveillance.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A system for monitoring concentration of one or more gases, comprising:
   a network of autonomous beacons, each beacon configured to activate at specified time intervals and transmit a laser beam at low transmission power levels to a receiving geostationary orbit (GEO) satellite,
   wherein
   each beacon is further configured to transmit the laser beam through a same atmospheric column to allow noise caused by atmospheric turbulence to be averaged out, and
   the receiving GEO satellite comprises a sensor configured to receive the laser beam from at least one activated beacon to generate raw gas concentration data based on the received laser beam.

2. The system of claim 1, wherein each beacon further comprises:
   a power unit configured to receive power from solar cells and power the beacon at low power;
   a communication unit configured to receive an activation signal from a node in order to activate the beacon for measuring gas concentration; and
   a global positioning unit configured to transmit a location identifier of the beacon to the node.

3. The system of claim 2, wherein the communication unit is configured to receive the activation signal based on the availability of the receiving GEO satellite, suspected gas emissions violations at one or more sites, operation of beacons in a surrounding region, and/or weather and/or cloud forecasts over regions.

4. The system of claim 1, wherein each beacon further comprises:
   a laser unit configured to transmit the laser beam with two frequencies of light to the receiving GEO satellite when an activation signal is received by the beacon; and
   a pointing unit configured to align the laser beam to point to a sensor on the receiving GEO satellite.

5. The system of claim 4, wherein each beacon further comprises:
   an aperture cover operatively connected to the laser unit, and configured to cover a lens of the laser unit to protect the laser unit from dust and moisture and open when the beacon is activated.

6. The system of claim 1, wherein the receiving GEO satellite further comprises:
   a sensor configured to receive the laser beam from the one or more activated beacons; and
   a communication unit configured to transmit the raw gas concentration data to a node for processing of the raw gas concentration data.

7. The system of claim 6, wherein the node is configured to process the raw gas concentration data to determine a concentration level of a gas in an atmospheric column through which the laser beam passed.

8. An apparatus, comprising:
   a laser unit configured to activate at specified time intervals based on a command received from an electrical unit and, when activated, generate a laser beam to be transmitted to a geostationary orbit (GEO) satellite in order to measure concentration of a gas in an atmospheric column through which the laser beam passes, wherein
   the laser beam is configured to pass through a same atmospheric column to allow noise caused by atmospheric turbulence to be averaged out.

9. The apparatus of claim 8, wherein the electrical unit further comprises:
   a global positioning unit configured to transmit a location of the apparatus via a transmitter operatively connected to the global positioning unit.

10. The apparatus of claim 8, wherein the electrical unit further comprises:
    a receiver configured to receive a command from a node to activate the apparatus for gas concentration monitoring; and
    a controller configured to command the laser unit to generate the laser beam for the gas concentration monitoring.

11. The apparatus of claim 10, wherein the receiver is configured to receive the command via a cellular, WIFI or other network connection.

12. The apparatus of claim 8, wherein the electrical unit further comprises:
a power unit operatively connected to solar cells,
wherein the solar cells are configured to maintain charge to the power unit, and the power unit is configured to power the apparatus.

13. The apparatus of claim 8, further comprising:
a laser alignment unit configured to align the laser beam generated from the laser unit and direct the laser beam to the GEO satellite.

14. The apparatus of claim 8, wherein the laser unit is further configured to generate simultaneously or alternatively a first frequency and a second frequency for a molecule of interest and combine the first frequency and the second frequency into the generated laser beam.

15. The apparatus of claim 14, wherein the first frequency is tuned to a molecular absorption frequency and the second frequency is tuned to be off by a molecular resonance from the molecular absorption frequency.

16. The apparatus of claim 8, further comprising:
an aperture cover operatively connected to the laser unit, and configured to cover a lens of the laser unit to protect the laser unit from dust and moisture and open when the apparatus is activated.

17. A method for monitoring concentration of one or more gases, comprising:
receiving an activation signal from a node for monitoring the concentration of the one or more gases; and
transmitting a laser beam from an autonomous beacon to a receiving geostationary orbit (GEO) satellite in order to determine the concentration level of the one or more gases in an atmospheric column through which the laser beam passes, wherein
the laser beam is configured to pass through a same atmospheric column to allow noise caused by atmospheric turbulence to be averaged out.

18. The method of claim 17, further comprising:
generating simultaneously or alternatively a first frequency and a second frequency for a molecule of interest; and
combining the first frequency and the second frequency to create the laser beam.

19. The method of claim 18, wherein the first frequency is tuned to a molecular absorption frequency and the second frequency is tuned to off by a molecular resonance from the molecular absorption frequency.

20. The method of claim 17, further comprising:
aligning the laser beam to accurately transmit the laser beam to the receiving GEO satellite.

21. A system, comprising:
a plurality of autonomous beacons proximate to emission sources;
at least three geostationary (GEO) satellites, each GEO satellite comprises a sensor to provide continuous coverage for the emission sources; and
a central node configured to receive data from the at least three satellites, wherein
each of the plurality of autonomous beacons is configured to transmit laser beams to a sensor on one of the at least three satellites, and
each of the at least three GEO satellites is further configured to
measure gas densities in atmosphere originating from one of a plurality of emission sources located within a coverage footprint of the sensor, and
average out fluctuations in the laser beams during time intervals when clouds do not block passage of the laser beams, the fluctuation caused by naturally occurring atmospheric turbulence within fixed narrow columns of the atmosphere, each of the fixed narrow columns of the atmosphere extending from each of the plurality of autonomous beacons to one of the at least three GEO satellites through which the laser beams pass.

\* \* \* \* \*